US006579352B1

(12) United States Patent
Tanaka et al.

(10) Patent No.: US 6,579,352 B1
(45) Date of Patent: Jun. 17, 2003

(54) AIR CLEANING FILTER

(75) Inventors: Atsuo Tanaka, Kyoto (JP); Kazuro Isomae, Kanagawa (JP); Mikiko Gokano, Kanagawa (JP)

(73) Assignee: Nikki-Universal Co., Ltd., Tokyo (JP)

( * ) Notice: Subject to any disclaimer, the term of this patent is extended or adjusted under 35 U.S.C. 154(b) by 0 days.

(21) Appl. No.: 09/230,114

(22) PCT Filed: Jul. 24, 1997

(86) PCT No.: PCT/JP97/02555

§ 371 (c)(1), (2), (4) Date: Jan. 22, 1999

(87) PCT Pub. No.: WO98/04334

PCT Pub. Date: Feb. 5, 1998

(30) Foreign Application Priority Data

Jul. 25, 1996 (JP) ........................................ 8-196288

(51) Int. Cl.[7] ........................ B01D 45/00; A61L 9/00; C12N 11/14

(52) U.S. Cl. ............................ 96/226; 422/4; 422/28; 442/123; 435/176; 435/177; 435/180

(58) Field of Search ............................ 96/226; 422/1, 422/4, 28; 442/118, 123; 435/174–182

(56) References Cited

U.S. PATENT DOCUMENTS 3,519,538 A * 7/1970 Messing
3,968,297 A 7/1976 Sauer
4,006,059 A * 2/1977 Butler ........................ 435/176
4,033,817 A * 7/1977 Gregor ........................ 435/175
4,247,642 A * 1/1981 Hirohara et al. ............ 435/178
4,251,631 A * 2/1981 Simon ........................ 435/106
4,493,894 A * 1/1985 Miyashiro
4,748,121 A * 5/1988 Beaver
4,749,390 A * 6/1988 Burnett ........................ 55/316
4,749,653 A * 6/1988 Lee et al. .................... 435/176
5,021,345 A * 6/1991 Urban et al. ................ 435/135
5,051,184 A * 9/1991 Taylor ........................ 210/632
5,055,113 A * 10/1991 Larson ........................ 51/298
5,098,417 A * 3/1992 Yamazaki et al. .......... 424/445
5,102,799 A * 4/1992 Urban et al. ................ 435/134
5,130,237 A * 7/1992 Thomas et al. .............. 426/50
5,395,411 A * 3/1995 Kobayashi .................. 55/486
5,527,672 A * 6/1996 Mansfield et al. ......... 427/2.11
5,614,105 A * 3/1997 Heilmann et al. .......... 210/490
5,620,706 A * 4/1997 Dumitriu
5,719,228 A * 2/1998 Taylor ........................ 524/593
5,889,073 A * 3/1999 Zhang et al. ................ 522/3
6,228,135 B1 * 5/2001 Sugo et al. ................ 423/210
6,372,472 B1 * 4/2002 Nehls et al. ................ 210/606
2002/0102180 A1 * 8/2002 Sheldon ...................... 422/4

FOREIGN PATENT DOCUMENTS

GB 1 486 305 9/1977
GB 1 503 879 3/1978
JP 2-41166 * 2/1990
JP 2-245190 * 9/1990

OTHER PUBLICATIONS

"Primary Containment of Biohazards," Office of Health and Safety, Centers for Disease Control and Prevention, last reviewed May 18, 2001, jttp://www.cdc.gov/od/ohs/biosfty/bsc/BSC2000sec2.htm.
"Filter Medium, Fire–Resistant, High–Efficiency," Military Specification, MIL–F–51079C, Mar. 14, 1985.

* cited by examiner

*Primary Examiner*—Chester T. Barry
(74) *Attorney, Agent, or Firm*—Fish & Richardson P.C.

(57) ABSTRACT

An air purifying filter having an enzyme immobilized on the surface of a carrier is capable of direct killing or otherwise control of air-borne microorganisms which have been difficult to control by means of the conventional air purifying filters; and the filter is also capable of removing the retained microorganisms by killing or otherwise controlling them.

46 Claims, 4 Drawing Sheets

AIR CLEANING FILTER

TECHNICAL FIELD

This invention relates to an air purifying filter having an enzyme immobilized on a surface of a carrier. The invention particularly relates to an air purifying filter having an enzyme immobilized on a surface of a HEPA filter which is composed of boron-silica glass fibers not rendered to be water repellent, ion-exchange fibers having functional groups or boron-silica glass fibers coated with a polymer having functional groups.

BACKGROUND ART

Various air purifiers (air cleaners) and air washers are known as apparatus for removing unwanted materials from air. Air purifiers (air cleaners) are apparatuses that primarily depend on air purifying filters (air filters) for filtering off unwanted materials in air such as suspended fine particles (e.g. dust) on which gaseous contaminants, fats/oils and microorganisms such as bacteria are occasionally deposited. Air washers are apparatus which typically involve the washing of air with water to remove dirt/dust particles, microorganisms, etc. from air.

The first mentioned air purifying filters are available in various types which have been developed to suit specific factors such as the material to be removed, its particle size and the efficiency of particle capture. The filters are also available in various shapes including mats, wedges, fold-ins, baskets, bags, panels and boxes. However, single use of the conventional air purifying filters has been unable to achieve complete removal of air-borne microorganisms such as molds, bacteria and fungi. Further, the microorganisms captured on the filters are difficult to control or kill and may grow on the filters and scatter about to cause secondary contamination; therefore, the existing air purifying filters have not necessarily given satisfactory results in the air purification treatment.

Under the circumstances, the present inventors thought of using enzymes effective in controlling or killing air-borne microorganisms such as mold, bacteria and fungi. Various techniques have so far been proposed as bacteriacidal/ sterilizing or antimicrobial means using enzyme and they include the following.

Japanese Patent Publication No. 21422/1979 discloses a method of controlling microorganisms (e.g. heat-resistant cell spores) in processed food which is characterized in that at least one member of the group consisting of urea, thioglycolic acid and mercaptoethanol, and a bacterial cell wall lysing enzyme are added to the food or starting materials thereof and the mixture is held for a specified time and subsequently heat treated.

Japanese Patent Public Disclosure No. 30584/1989 describes a biocatalyst immobilizing carrier for typical use in the food industry which has a microorganism or an enzyme that work as a biocatalyst immobilized on a carrier together with a lysing enzyme. According to the patent, exemplary microorganisms include Gram-negative bacteria, Gram-positive bacteria, yeasts and molds; useful enzymes are hydrolases such as amylase, protease and lipase; lysing enzymes include lysozyme, endo-N-acetylmuramidase, endo-N-acetylglucosaminidase, autolysin, ensopeptidase-type bacterial cell wall lysing enzymes, amidase-type bacterial cell wall lysing enzymes, mold cell wall lysing enzymes and yeast cell wall lysing enzymes.

Japanese Patent Public Disclosure No. 5822/1990 discloses an alcoholic preparation for use on raw vegetable which incorporates egg white lysozyme as a natural antimicrobial agent and which has the pH adjusted to be within the range of 2.0–7.0, as well as a modifier for use on raw vegetable which incorporates an organic acid and an organic acid salt or a phosphate salt, has the pH adjusted to be within the range of 2.0–7.0 and also incorporates egg white lysozyme as an antimicrobial agent.

Japanese Patent Public Disclosure No. 23856/1990 discloses a food preservation method which, for the purpose of effectively preventing putrefaction and deterioration of food, adds a polyglycerin fatty acid ester, lysozyme and protamine to the food being produced.

Japanese Patent Publication No. 22144/1991 describes a method of food sterilization which comprises allowing a lysing enzyme such as lysozyme, kinase or $\beta$-1,6-glucanase to act upon food and then subjecting it to an ultrasonic treatment.

Japanese Patent Public Disclosure No. 76362/1993 describes a process for producing lysozyme-containing particles which comprises the steps of applying a spray of an aqueous lysozyme slurry into the reaction chamber of a fluidized-bed reactor together with the core particles of a hydratable substance, evaporating the residual water so that the dry lysozyme coating will remain on the particulate core substance, to thereby provide lysozyme-containing particles. The patent teaches that the thus produced lysozyme-containing particles are useful in various kinds of foods, cosmetics, medicines and other applications.

Japanese Patent Public Disclosure No. 276910/1993 discloses a food preservative characterized by the combination of protamine with at least one substance selected from the group consisting of lysozyme, an antimicrobial substance extracted from licorice, vitamin $B_1$ ester and a polyphosphate salt.

Japanese Patent Public Disclosure No. 217749/1994 discloses a food preservative which comprises a caprylic acid monoglyceride and/or a capric monoglyceride in combination with glycine, sodium acetate, lysozyme and an organic acid or an alkali salt thereof, as well as a food preservative which comprises a caprylic acid monoglyceride and/or a capric monoglyceride in combination with glycine, sodium acetate, lysozyme and polyphosphate salt. The patent also teaches that although lysozyme is said to have a lysing effect, its effectiveness is limited to some microbial strains and it cannot be claimed as a practically feasible bacteriostat if used alone.

Japanese Patent Public Disclosure No. 246157/1994 discloses a cell adsorber which has the denatured product of a protein such as lysozyme, avidin or trypsin immobilized on a water-insoluble carrier. According to the patent, cells can be effectively separated or removed from a cell-containing solution by using the cell adsorber.

Japanese Patent Public Disclosure No. 236479/1995 discloses the lysozyme binding of an antimicrobial compound selected from among plant-derived antimicrobial compounds (e.g. perillaldehyde, cinnamaldehyde, salicylaldehyde, anisaldehyde, benzaldehyde and vanillin), antibiotics, synthetic antimicrobial agents, etc. The patent teaches that lysozyme bound to these antimicrobial compounds is useful in medicines, quasi-drugs, foods, etc.

There have also been proposed various inorganic antimicrobial materials which have antimicrobial metals such as silver, zinc and copper supported on inorganic carriers. Examples are inorganic antimicrobial agents having silver, zinc and other ions supported on zeolite through ion-exchange, inorganic antimicrobial agents having metallic silver supported on calcium phosphate through adsorption, inorganic antimicrobial agents having silver ions supported on zirconium phosphate through ion-exchange, and inorganic antimicrobial agents having silver complex salts supported on amorphous silicon oxide through occlusion; these inorganic antimicrobial materials are applied to fibers, plastics, films, paints and various other products (ZEOLITE, vol. 13 No. 2 (1966), pp. 56–63).

Various carriers have also been proposed for use in immobilizing the aforementioned enzymes and they include the following.

Japanese Patent Public Disclosure No. 48825/1974 describes the use of phenolic and aliphatic amine-based ion-exchange resins as carriers for immobilizing egg white lysozyme.

Japanese Patent Public Disclosure No. 48080/1984 discloses the use of platinum coated with Amberlite or aminated polyvinyl alcohol and the like for complex immobilizing of more than one enzyme.

Japanese Patent Public Disclosure No. 49795/1985 discloses the use of nonwoven carriers composed of natural fibers or chemical fibers or mixtures thereof in the web for immobilization treatment of bactericidal lysing enzymes.

Japanese Patent Public Disclosure No. 30584/1989 teaches a column composed of ceramic honeycomb structures, a membrane, particles or a porous body as biocatalyst immobilizing carrier and one which is formed of cordierite is specifically described.

Japanese Patent Public Disclosure No. 256388/1989 teaches the use of an anion-exchange resin as a carrier for supporting inulin-D-fructotransferase.

Japanese Patent Public Disclosure No. 39239/1990 discloses the use of a porous anion-exchange resin as an enzyme immobilizing carrier which has either primary amino groups or secondary amino groups or both as exchange groups.

Japanese Patent Public Disclosure No. 41166/1990 teaches that a porous membrane, fibers or spun yarns of ceramics, glass or organic polymers, as well as nets formed by knitting such fibers or spun yarns or particles thereof are suitable as enzyme-immobilizing carriers.

Japanese Patent Public Disclosure No. 269362/1991 teaches the use of latices as carriers in immunological assay reagents.

Japanese Patent Public Disclosure No. 91117/1994 discloses an air purifier having both a slime bacterial filter and a filter based on an antimicrobial polymer. The patent also teaches the typical use of polyurethane forms, polyethylene, polystyrene, polyacrylamides and/or various photo-crosslinkable or photocurable synthetic polymers as the base for immobilizing slime bacteria produced lysing enzymes and antibiotics.

As outlined above, it has bee proposed in various fields such as food, medicines and cosmetics that enzymes, for example, those having a lysing action as exemplified by lysozyme be used in solution for bactericidal, antimicrobial, preservative, antimold and other purposes.

However, no technical means has ever been proposed in the art that is based on the idea that an air purifying filter made of a specified material can be enhanced in its ability to control, kill or otherwise remove microorganisms by combining the filter with the above-mentioned enzymes having a lysing action.

The present inventors conducted intensive studies by making approaches from various viewpoints in order to enhance the ability of an air purifying filter to control, kill or otherwise remove microorganisms by using it in combination with a lysing enzyme either alone or in the copresence of various proteins, peptides, polysaccharides, etc. As a result, the inventors found that by immobilizing enzymes on the surfaces of carriers which are made of specified materials and which have specified shapes, the ability of the air purifying filter to control, kill or otherwise remove microorganisms could be enhanced and maintained for a prolonged period. The present invention has been accomplished on the basis of this finding.

Disclosure of Invention

The invention provides an air purifying filter having an enzyme immobilized on the surface of a carrier.

The invention also provides an air purifying filter having a large amount of enzyme immobilized on the surfaces of non-water repellent boron-silica glass fibers through covalent bonding and/or ionic bonding.

The invention further provides an air purifying filter which has a large amount of enzyme immobilized on a HEPA filter through covalent bonding and/or ionic bonding, said HEPA filter being based on non-water repellent microfine boron-silica glass fibers having a diameter of no more than 4 $\mu$m.

The invention also provides an air purifying filter having a large amount of enzyme dispersed and immobilized on the surfaces of radical-having ion-exchange fibers through ionic bonding.

Further in addition, the invention provides an air purifying filter characterized on that a large amount of enzyme is dispersed and immobilized, through ionic bonding, on the surfaces of boron-silica glass fibers coated with a polymer having radicals or functional groups.

BEST MODE FOR CARRYING OUT THE INVENTION

Figure 1:
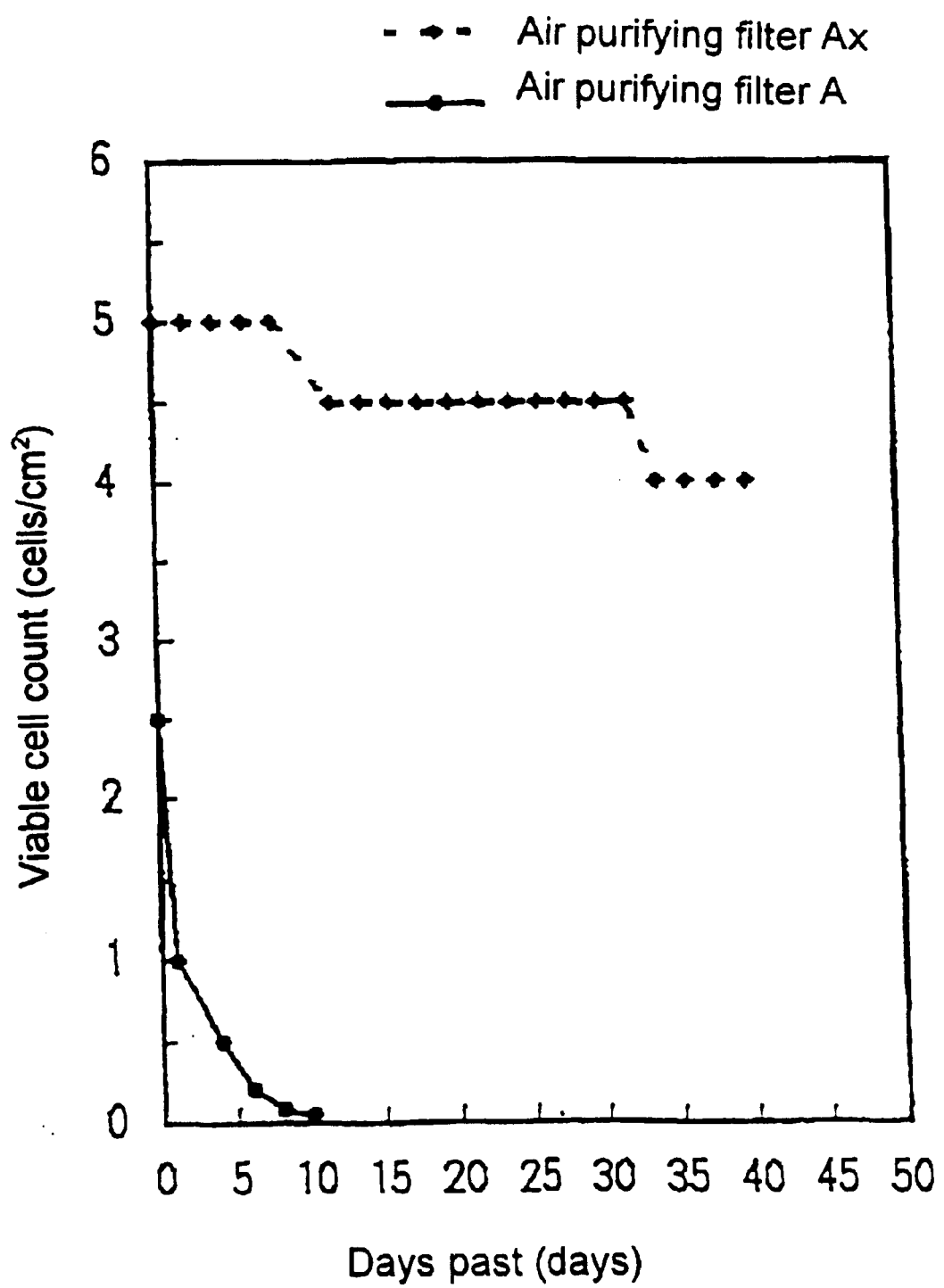
FIG. 1 is a graph showing the time-dependent changes in the number of viable cells of a microorganism which was captured with a prior art air purifying filter (air purifying filter Ax of comparative Example 1) and an air purifying filter according to the invention (air purifying filter A of Example 1)
Figure 2:
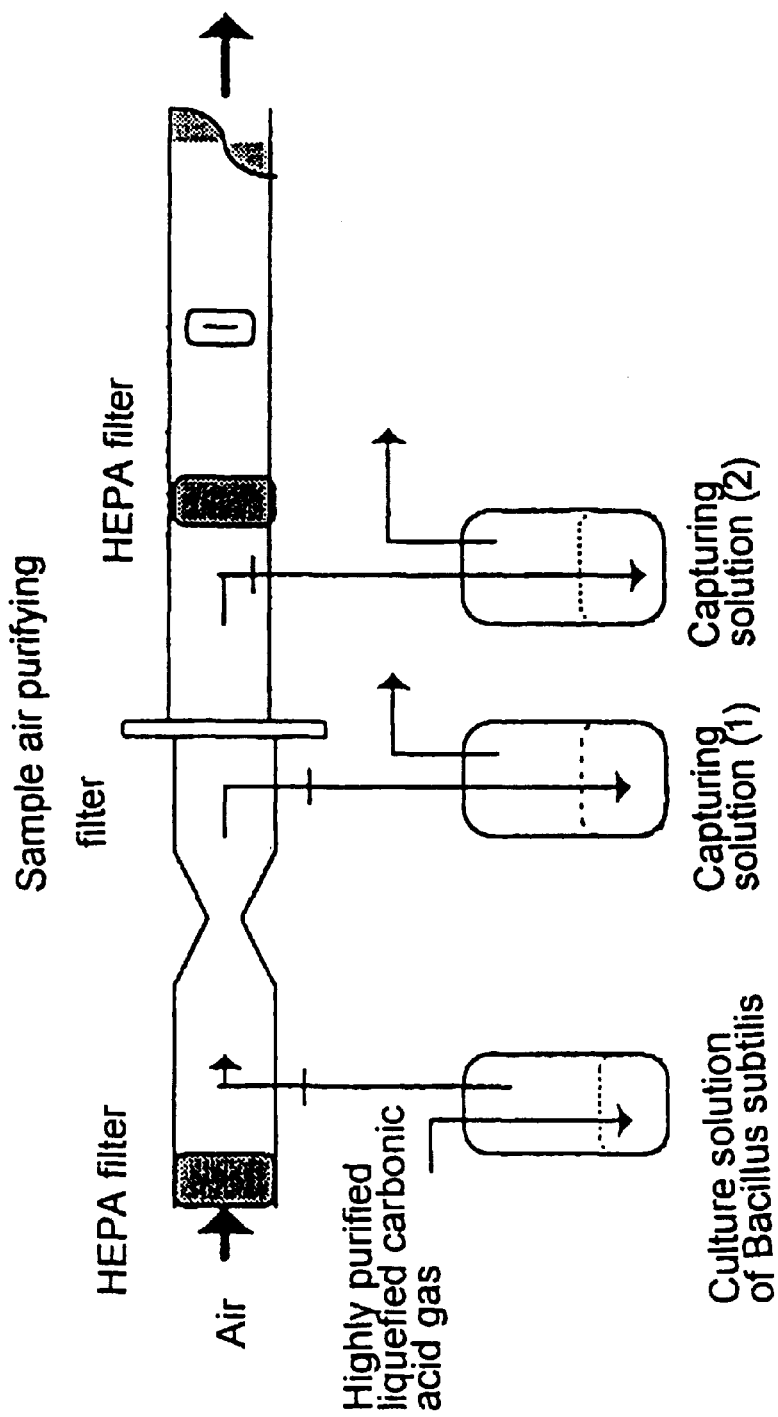
FIG. 2 is a schematic view of the air-borne microorganism measuring apparatus used to evaluate the effectiveness of the air purifying filters used in specified tests.

The constituent material for the carrier of the air purifying filter according to the invention is not limited in any particular way as long as it is capable of performing as an air purifying filter; examples include various organic fibers and inorganic fibers such as cellulose fibers, asbestos fibers, glass fibers and non-glass synthetic fibers such as ion-exchange fibers, and they may be used in different applications depending upon the characteristics of their origin.

Among glass fibers, boron-silica glass fibers have adequate strength in fiber diameters of 4 $\mu$m and less and, hence, are suitable for fabricating high-performance filters capable of efficient capture.

In order to ensure that a large amount of enzyme is effectively immobilized on fibers, it is preferred to use boron-silicate glass fibers not rendered to be water-repellent. Also preferred to use are ion-exchange fibers having functional groups, as well as glass fibers, preferably, boron-silicate glass fibers, which are coated with a polymer having functional groups. There are no particular limitations on the functional groups that can be used and preferred examples are —NHR (R is not H but an alkyl group which is either methyl, ethyl, propyl selected from between n-propyl and i-propyl, or butyl selected from among b-butyl, s-butyl, i-butyl and t-butyl), —NH$_2$, —C$_6$H$_5$NH$_2$, —CHO, —COOH, —OH, etc.

The shape of the air purifying filter is not limited in any particular way and it may be cotton-like as in the form of a nonwoven cloth, or it may assume any other shapes including filter paper, honeycombs, particles and screens. The honeycomb may take any cellular form which may be polygonal (e.g. triangular, rectangular, pentagonal and hexagonal) or corrugated. A preferred example is described in Japanese Patent Public Disclosure No. 15028/1984 and it is an assembly of ceramic fibers (HONEYCLE carrier), in which sheet-like assemblies of ceramic fibers selected from among inorganic fibers such as silica fibers, alumina fibers, aluminosilicate fibers and zirconia fibers which are bound together with silica gel are staked to form honeycombs, thereby producing a honeycomb structure.

In particular, a HEPA filter which was developed as part of the post-war projects of nuclear technology development by making use of the "depth filtration" principle and which is based on microfine glass fibers ($\leq 4$ $\mu$m in diameter), reinforced with a small amount (typically no more than 7%) of chopped strand glass fibers and bound together with an organic binder typically contained in no more than 7% is a preferred carrier material since it far excels other filters in terms of low-pressure loss characteristics, high arrest efficiency and high physical strength. HEPA filters include a high-performance filter capable of arresting at least 99.97% of 0.3 m DOP particles, a quasi-high performance HEPA filter capable of arresting at least 95%–99% of 0.3 $\mu$m DOP particles and an ULPA filter of which the arresting performance has been enhanced to an ultrahigh level.

The enzymes to be used in the invention are not limited in any particular way as long as they have a lysing action; lysozyme, chitinase, protease, glucose oxidase, glucanase, endo-β-N-acetylgluco-saminidase and endolysin may be mentioned as enzymes having the preferred lysing action; and one or more of these enzymes may be used either alone or in combination with non-enzyme proteins or peptides having a bactericidal action or with poly-saccharides.

Examples of the proteins and peptides having a bactericidal action include protamine, lactoferrin and polylysine.

Enzymes, particularly lysozyme, are capable of efficient glycosylation with polysaccharides through chemical covalent bonding to exhibit a marked antimicrobial action. Exemplary polysaccharides include glucan, dextran, mannan, galactomannan, laminaran, carrageenan and agarose. One or more of these polysaccharides may be used.

Examples of mixtures or chemical compounds of enzymes with other proteins or peptides include the lysozyme/protamine and lysozyme/apolactoferrin combinations.

Examples of the mixtures or chemical compounds of enzymes with polysaccharides include the lysozyme/glucan and lysozyme/galactomannan combinations.

The air purifying filter of the invention can be used in various consumer and industrial situations that require air purification. In particular, it finds optimal use in semiconductor-, food- and hospital-related facilities and the like. With the air purifying filter of the invention, air-borne bacteria and fungi which have defied effective treatment with the existing air purifying filters, in particular, Bacillus subtilis, Micrococcus luteus, Staphylococci, Streptococci and other microorganisms that are resistant to dryness and which remain air-borne for a prolonged time, can be controlled, killed or otherwise removed by direct lysis reaction to purify the air. An added advantage of the air purifying filter of the invention concerns microorganisms such as long rods which have very small cross-sectional areas; if the microorganisms captured by the conventional air purifying filters are very small, they may occasionally slip out of the pores in the filter through their own peristalsis in contrast, and the microorganisms captured on the air purifying filter of the invention will be killed or otherwise controlled by the lysing action of the enzyme and will no longer slip out of the pores in the filter. As a further problem, a conventional air purifying filter which is incapable of effective control of the captured microorganisms has the potential to cause secondary contamination of air as the result of regrowth and scattering about of the captured microorganisms; in contrast, the air purifying filter of the invention continues to exhibit satisfactory lysing action on the retained microorganisms and by killing or otherwise controlling such microorganisms effectively, secondary contamination of air can be prevented for a prolonged time.

EXAMPLES

The present invention will now be described below in greater detail with reference to Examples, Comparative Examples and Tests. It should, however, be noted that the invention is in no way limited by those Examples.

Example 1

HEPA filter of Nippon Muki Co., Ltd. (trade name: ATOMOS) having a high arrest efficiency of at least 99.97% in a 0.3 $\mu$m monodisperse DOP test was immersed in a toluene solution of 10% γ-aminopropyl triethoxysilane at room temperature for 12 hours, washed with toluene and air dried at room temperature to produce a silanylated HEPA filter. The silanylated HEPA filter was immersed in a 1% aqueous glutaraldehyde solution at room temperature for 6 hours so that aldehyde groups were introduced into the surfaces of the silanylated HEPA filter. Thereafter, the filter was washed with water and left in a 50 mM acetate buffer solution containing 1% protamine and 1% lysozyme for 24 hours. Thereafter, the HEPA filter to which the protamine and lysozyme were immobilized was further washed with a buffer solution prepared by mixing a 500 mM NaCl solution with a 500 mM acetic acid solution. Upon air drying, the physical adsorption of the enzyme on the HEPA filter was removed to leave only the protamine and lysozyme contents that were immobilized through covalent bonding. The thus prepared filter was designated as air purifying filter A.

Comparative Example 1

The untreated HEPA filter which was used in Example 1 was designated as air purifying filter Ax.

Comparative Example 2

The HEPA filter used in Example 1 was silanylated and had aldehyde groups introduced into the surfaces as in Example 1 to thereby prepare air purifying filter Ay.

Example 2

The procedure of Example 1 was repeated, except that the carrier HEPA filter was replaced by an air conditioning resin-bonded nonwoven fabric filter (product of TOYOBO CO., LTD.). Thus, air purifying filter B was prepared that had only protamine and lysozyme left immobilized through covalent bonding.

Comparative Example 3

The untreated air conditioning resin-bonded nonwoven fabric filter used in Example 2 was designated as air purifying filter Bx.

Comparative Example 4

The air conditioning resin-bonded nonwoven fabric filter used in Example 2 was silanylated and had aldehyde groups introduced into the surfaces as in Example 2 to thereby prepare air purifying filter By.

Example 3

The procedure of Example 1 was repeated, except that the carrier HEPA filter was replaced by a honeycomb carrier (tradename: "HONEYCLE" of NICHIAS CORP.) which was prepared by stacking sheets of ceramic fibers to form 600 honeycomb cells. Thus, air purifying filter C was prepared as in Example 1 that had only protamine and lysozyme left immobilized through covalent bonding.

Comparative Example 5

The untreated honeycomb carrier used in Example 3 was designated air purifying filter Cx.

Comparative Example 6

The honeycomb carrier used in Example 3 was silanylated and had aldehyde groups introduced into the surfaces as in Example 3 to thereby prepare air purifying filter Cy.

Test 1

A sample air purifying filter unit (200 mm×200 mm×150 mm) was placed in a closed 100-L apparatus for testing air-borne microorganism removing performance and the air within the apparatus which contained $1 \times 10^5$ air-borne microorganism cells per 100-L was circulated at a flow rate of 10-L per minute by means of a blower. After a specified time of circulation treatment, the air-borne microorganism cells in the test apparatus were collected on an agar medium and cultured aerobically at a temperature of 30° C. for 120 hours. Thereafter, the number of viable cells in 100-L of the sample air was visually counted. The results are shown in Tables 1–6.

TABLE 1

| | No. of Viable Cells (per 100 L) |
|---|---|
| Example 1 | ≦10 |
| Comp. Ex. 1 | 100 |
| Comp. Ex. 2 | 100 |

Table 1 shows the results of the 24 hours circulation treatment with the air purifying filter of Example 1 as well as the air purifying filters Ax and Ay of Comparative Examples 1 and 2, respectively.

TABLE 2

| | No. of Viable Cells (per 100 L) |
|---|---|
| Example 1 | ≦10 |
| Comp. Ex. 1 | 300 |
| Comp. Ex. 2 | 300 |

Table 2 shows the results of the 2 hours circulation treatment with the air purifying filter A of Example 1 as well as the air purifying filters Ax and Ay of Comparative Examples 1 and 2, respectively.

As is clear from Tables 1 and 2, the HEPA filter having no enzymes immobilized thereto also showed high physical performance in trapping microorganism cells; however, the air purifying filter of the invention which had protamine and lysozyme immobilized through covalent bonding had at least 10 times greater purification performance in killing the microorganism cells by adsorbing them and lysing their cell walls with the aid of the immobilized lysozyme.

TABLE 3

| | No. of Viable Cells (per 100 L) |
|---|---|
| Example 2 | ≦10 |
| Comp. Ex. 3 | 3000 |
| Comp. Ex. 4 | 3000 |

Table 3 shows the results of the 24 hours circulation treatment with the air purifying filter B of Example 2 as well as the air purifying filters Bx and By of Comparative Examples 3 and 4, respectively.

TABLE 4

| | No. of Viable Cells (per 100 L) |
|---|---|
| Example 2 | ≦10 |
| Comp. Ex. 3 | 8000 |
| Comp. Ex. 4 | 8000 |

Table 4 shows the results of the 2 hours circulation treatment with the air purifying filter B of Example 2 as well as the air purifying filters Bx and By of Comparative Examples 3 and 4, respectively.

As is clear from Tables 3 and 4, the air purifying filter of the invention which had protamine and lysozyme immobilized on the air conditioning resin-bonded nonwoven fabric filter which was initially low in microorganism trapping performance exhibited at least 300 times as great purification performance in killing the microorganism cells as the air conditioning resin-bonded nonwoven fabric filter which had no enzymes immobilized thereto.

TABLE 5

| | No. of Viable Cells (per 100 L) |
|---|---|
| Example 3 | ≦30 |
| Comp. Ex. 5 | 10000 |
| Comp. Ex. 6 | 10000 |

Table 5 shows the results of the 24 hours circulation treatment with the air purifying filter C of Example 3 as well as the air purifying filters Cx and Cy of Comparative Examples 5 and 6, respectively.

TABLE 6

| | No. of Viable Cells (per 100 L) |
|---|---|
| Example 3 | ≤100 |
| Comp. Ex. 5 | 10000 |
| Comp. Ex. 6 | 10000 |

Table 6 shows the results of the 2 hours circulation treatment with the air purifying filter C of Example 3 as well as the air purifying filters Cx and Cy of Comparative Examples 5 and 6, respectively.

As is clear from Tables 5 and 6, the air purifying filter of the invention which had protamine and lysozyme immobilized on the honeycomb carrier which was fabricated by stacking sheets of ceramic fibers in honeycombs which were hardly capable of trapping microorganism cells exhibited at least 100 times as great purification performance by killing the microorganism cells as the air conditioning honeycomb carrier which had no enzymes immobilized thereto.

Test 2

A 200 mm×200 mm section was taken from each of the air purifying filter A of Example 1 and the air purifying filter Ax of Comparative Example 1 and each section was placed in a filter holder in an experimental duct, through which air containing 210 air-borne microorganism cells in every 30-L challenge was supplied at a flow rate of 30 L per minute by means of a blower; thereafter, each air purifying filter was stored at room temperature in a desiccator held at a relative humidity of 60%; and a portion of each filter was taken at given time intervals and the number of viable cells as captured by the filter was counted by a poured culture method. The results are shown in FIG. 1, which is a graph depicting the survival curve of the trapped viable cells; the vertical axis of the graph plots the viable cell count (cells/cm$^2$) and the horizontal axis plots the days past. As is clear from FIG. 1, the viable cells retained on the air purifying filter A of Example 1 of the invention which had the enzyme immobilized thereon decreased rapidly in number and one week later, few viable cells could be detected. In contrast, the viable cells retained on the air purifying filter Ax of Comparative Example 1 decreased only slightly in number and most of them remained when one month had passed. Thus, it was supported that the air purifying filter of the invention which had the enzyme immobilized thereon was capable of air purification by killing the captured microorganism cells.

Example 4

A filter paper-like carrier for use in a pseudo-HEPA filter (product of HOKUETSU PAPER MILLS, LTD.) which was composed of boron-silica glass fibers not rendered to be water repellent and which had an arrest efficiency of at least 99% in a 0.3 μm monodisperse DOP test was immersed in a toluene solution of 10% γ-aminopropyl triethoxysilane at room temperature for 12 hours, washed with methanol and air dried at room temperature to produce a silanylated filter paper-like carrier. The silanylated filter-paper like carrier was immersed in a 2.5% aqueous glutaraldehyde solution at room temperature for 1 hour so that aldehyde groups were introduced into the silanylated filter paper-like carrier. The filter paper-like carrier into which the aldehyde groups were introduced was washed with water; further washed with a buffer solution (pH 7) prepared by mixing a 500 mM NaCl solution with a 500 mM acetic acid solution; thereafter, was immersed in a 1% lysozyme-containing aqueous solution (S1) for 3 hours so as to immobilize the lysozyme. The filter paper-like carrier having the lysozyme immobilized thereon was further washed with a buffer solution of pH 7 (S2) prepared by mixing a 500 mM NaCl solution with a 500 mM acetic acid solution. Upon air drying, the physical adsorption of the enzyme on the filter paper-like carrier was removed to leave only the lysozyme content that was immobilized through covalent bonding. The thus prepared filter was designated as air purifying filter D1.

Example 5

The procedure of Example 4 was repeated, except that the aqueous solution (S1) was replaced by an aqueous solution containing 1% protamine and 1% lysozyme. Thus, air purifying filter D2 was prepared that had only protamine and lysozyme left immobilized through covalent bonding.

Example 6

The procedure of Example 4 was repeated, except that the aqueous solution (S1) was replaced by an aqueous solution containing 0.2% glucan and 1% lysozyme. Thus, air purifying filter D3 was prepared that had only glucan and lysozyme left immobilized through covalent bonding.

Example 7

The procedure of Example 4 was repeated, except that the aqueous solution (S1) was replaced by an aqueous solution containing 1% protamine, 0.2% glucan and 1% lysozyme. Thus, air purifying filter D4 was prepared that had only protamine, glucan and lysozyme left immobilized through covalent bonding.

Comparative Example 7

The untreated filter paper-like carrier for use in a pseudo-HEPA filter which was used in Example 4 and composed of the boron-silica glass fibers not rendered to be water repellent was designated air purifying filter Dx.

Example 8

A filter paper-like carrier for common use in a pseudo-HEPA filter (product of HOKUETSU PAPER MILLS, LTD.) which was composed of boron-silica glass fibers rendered to be water repellent was processed as in Example 4 to prepare air purifying filter El which had only lysozyme left immobilized through covalent bonding.

Example 9

The procedure of Example 8 was repeated, except that the aqueous solution (S1) was replaced by an aqueous solution containing 1% protamine and 1% lysozyme. Thus, air purifying filter E2 was prepared that had only protamine and lysozyme left immobilized through covalent bonding.

Example 10

The procedure of Example 8 was repeated, except that the aqueous solution (S1) was replaced by an aqueous solution containing 0.2% glucan and 1% lysozyme. Thus, air purifying filter E3 was prepared that had only glucan and lysozyme left immobilized through covalent bonding.

Example 11

The procedure of Example 8 was repeated, except that the aqueous solution (S1) was replaced by an aqueous solution containing 1% protamine, 0.2% glucan and 1% lysozyme. Thus, air purifying filter E4 was prepared that had only protamine, glucan and lysozyme left immobilized through covalent bonding.

Comparative Example 8

The untreated filter paper-like carrier for use in a pseudo-HEPA filter which was used in Example 8 and composed of the boron-silica glass fibers rendered to be water repellent was designated as air purifying filter Ex.

Test 3

The amounts of residual protamine and/or lysozyme in the spent aqueous solution (S1A) resulting from the immobilization treatments in Examples 4, 5, 6 and 7, as well as the amounts of protamine and/or lysozyme eluted into the buffer solutions (S2A) used to wash the filter paper-like carriers after immobilization were measured with a protein assay kit of Bio-Rad Laboratories at wavelength of 595 nm using a spectrophotometer model UV-2100PC of Shimadzu Corp. The percent immobilization of protamine and/or lysozyme through covalent bonding to the prepared air purifying filters was calculated, and the results are shown in Table 7.

Test 4

A culture solution of Bacillus subtilis (ATCC 6633) cells (count: $1\times10^3$ cells/mL) was atomized at a flow rate of 0.1 mL per minute by means of high-purity carbon dioxide gas supplied from a liquefaction container at a flow rate of 20 L per minute, and the atomized gas was mixed with clean air supplied through a HEPA filter at a flow rate of 80 L per minute to thereby prepare a sample gas. The sample gas was introduced at a flow rate of 100 L per minute into an air-borne microorganism measuring apparatus fitted with an air purifying filter sample and an accelerated test was conducted to evaluate the filter's bactericidal performance, with the introduction time set at 2 hours or 24 hours. For the last one hour of each introduction time, 25% of the sample gas which was yet to pass through the air purifying filter sample and 25% of the sample gas which had passed through it were collected in the inflow and the outflow, respectively. Both the inflow and the outflow were diluted 600 folds and 10 mL of each dilution was transplanted in a culture medium and cultured aerobically at a temperature of 37° C. for 48 hours, and then the number of colonies (CO) from the inflow (prior to the passage through the air purifying filter sample) and the number of colonies (Cs) from the outflow (after the passage through the air purifying filter sample) were counted respectively and the percent residual microorganism cells (C) in the sample gas after the passage through the air purifying filter sample was determined for each of the test times by the following formula:

$(Cs/SO)\times100=C(\%)$.

The results are shown in Tables 7–11.

Test 5

After the introduction of each sample gas in Test 4, clean air from the HEPA filter in place of the sample gas was introduced for one hour at a flow rate of 100 L per minute into the air-born cell measuring apparatus fitted with the air purifying filter sample; immediately thereafter, the air purifying filter sample was dismounted from the airborne-cell measuring apparatus; a section of size 1 cm² was taken from five sites of the air purifying filter sample, top, bottom, left, right and center; each section was directly transferred into a culture medium and cultured aerobically at a temperature of 37° C. for 48 hours; and thereafter, the number of colonies was counted at the five sites and the total was substituted for the number of viable cells in each 5 cm² area of the air purifying filter sample. The results for each test time are shown in Tables 7–11.

TABLE 7

| | Enzyme immobilization to filter, % | Residual cells in sample gas after passage through filter, % sample gas introduction time, hour | | No. of viable cells on filter (cells/5 cm²) Sample gas Introduction Time, hour | |
|---|---|---|---|---|---|
| | | 2 | 24 | 2 | 24 |
| Example 4 | 92 | <0.01 | <0.01 | <3 | <3 |
| Example 5 | 99 | <0.01 | <0.01 | <3 | <3 |
| Example 6 | 98 | <0.01 | <0.01 | <3 | <3 |
| Example 7 | 99 | <0.01 | <0.01 | <3 | <3 |
| Comparative Example 7 | — | 3.4 | 3.9 | >300 | >300 |
| Example 8 | 9 | 0.5 | 0.5 | 47 | >300 |
| Example 9 | 9 | 0.4 | 0.4 | 39 | >300 |
| Example 10 | 9 | 0.4 | 0.4 | 37 | >300 |
| Example 11 | 9 | 0.4 | 0.4 | 32 | >300 |
| Comparative Example 8 | — | 3.3 | 3.9 | >300 | >300 |

As is clear from the values of percent enzyme immobilization shown in Table 7, the air purifying filters D1, D2, D3 and D4 of Examples 4–7 employing the filter paper-like carrier for use in a pseudo-HEPA filter which was composed of boron-silica glass fibers not rendered to be water repellent featured at least 10 times more enzyme immobilization through covalent bonding than the air purifying filters E1, E2, E3 and E4 of Examples 8–11 which employed the filter paper-like carrier for use in a pseudo-HEPA filter which was composed of boron-silica glass fibers rendered to be water repellent. Thus, it was supported that the boron-silica glass fibers not rendered to be water repellent permitted high-volume enzyme immobilization through covalent bonding.

Table 7 also shows the data for the percent residual cells in the sample gas from the air purifying filter as determined in Test 4 using the air purifying filters D1–D4 and E1–E4 of Examples 4–11, as well as the air purifying filters Dx and Ex of Comparative Examples 7 and 8, respectively. As is clear from the values of percent residual cells, the air purifying cells Dx and Ex of Comparative Examples 7 and 8 which employed the filter paper-like carrier for use in a pseudo-HEPA filter which had no enzyme immobilized thereon exhibited reasonably high cell trapping performance; however, the air purifying filters E1–E4 of Examples 8–11 of the invention which employed the filter paper-like carrier for use in a pseudo-HEPA filter which was composed of the boron-silica glass fibers rendered to be water repellent showed about 8 times greater purification performance by killing organism cells. It was also supported that the air purifying filters D1–D4 of Examples 4–7 of the invention which employed the filter paper-like carrier for use in a pseudo-HEPA filter which was composed of the boron-silica glass fibers not rendered to be water repellent showed at least 300 times greater purification performance by killing organism cells.

Table 7 also gives data for the number of viable cells per 5 cm² on the air purifying filter as determined in Test for the air purifying filters D1–D4, and E1–E4 of Examples 4–11, the air purifying filters as well as the air purifying filters Dx and Ex of Comparative Examples 7 and 8, respectively. As is clear from the values of viable cell count given in Table 7 for the air purifying filter after 2 hours supply of the sample gas, the air purifying filters Dx and Ex of Comparative Examples 7 and 8 which employed the filter paper-like carrier for a pseudo-HEPA filter which had no enzymes immobilized thereon lacked bactericidal purification performance and, hence, the trapped microorganism cells could not be effectively killed and many of them remained alive on the air purifying filter. In contrast, the air purifying filters E1–E4 of Examples 8–11 of the invention which were composed of the water-repellent boron-silica glass fibers having the enzyme immobilized thereon had at least 6 times greater purification performance by killing the microorganism cells captured on the air purifying filter than the air purifying filters Dx and Ex of Comparative Examples 7 and 8; in addition, the air purifying filters D1–D4 of Examples 4–7 of the invention which employed the filter paper-like carrier for a pseudo-HEPA filter which was composed of the non-water repellent boron-silica glass fibers which had the enzyme immobilized thereon had at least 100 times greater purification performance by killing the microorganism cells captured on the air purifying filter, verifying the rapid decrease in the number of cells captured on the air purifying filters. Further, the air purifying filters D1–D4 of the invention still maintained the bactericidal purification performance on the filters even after 24 hours of introduction of the sample gas, and it was thereby demonstrated that the microorganism cells retained on the air purifying filters could be controlled efficiently over a prolonged time.

The foregoing results of Tests 3–5 demonstrate: the air purifying filters of the invention having the enzyme immobilized thereon maintained high bactericidal purification performance by adsorbing microorganism cells and lysing their cell walls by means of the lysozyme immobilized through covalent bonding; and the immobilization of a large amount of lysozyme and the like effectively through covalent bonding contributed to maintaining even higher bactericidal purification performance over a prolonged time.

Figure 3:
FIG. 3 is an electron micrograph showing how microorganism cells were captured by an air purifying filter according to the invention (air purifying filter D1 of Example 4)
Figure 4:
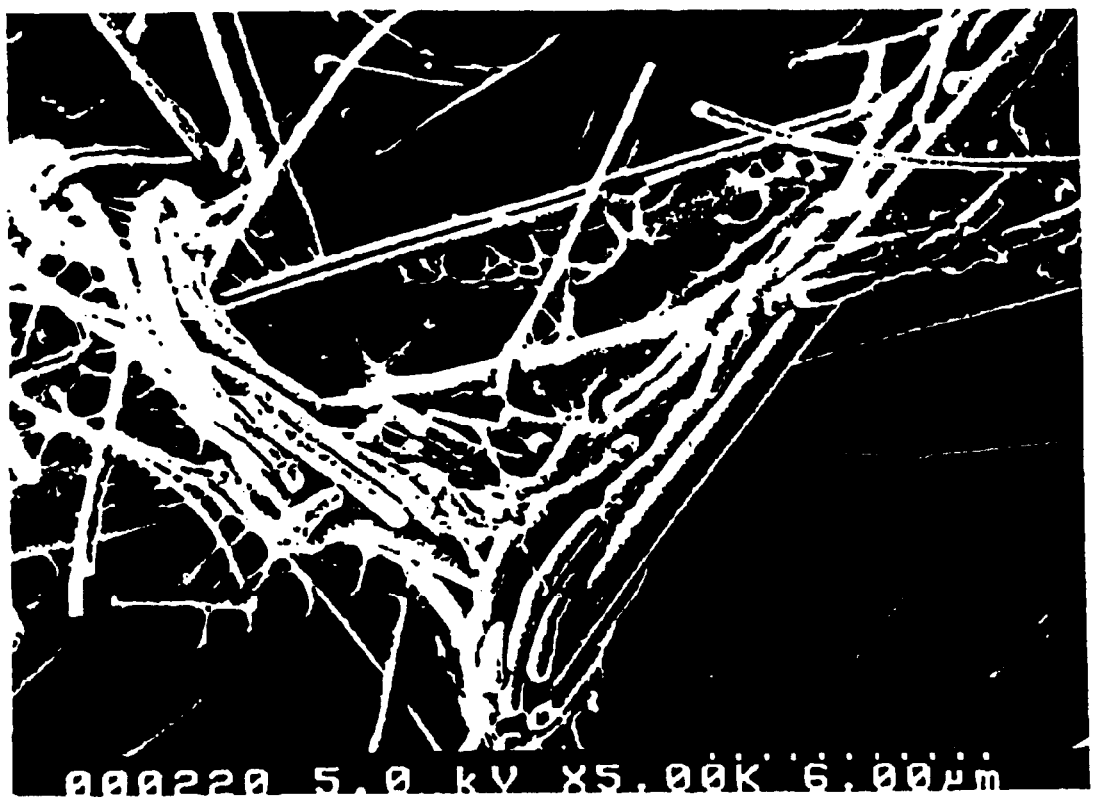
FIG. 4 is an electron micrograph showing how microorganism cells were captured by a prior art air purifying filter (air purifying filter Dx of Comparative Example 7).

The state of the microorganism cells trapped by the air purifying filter D1 of Example 4 of the invention which had the enzyme immobilized thereon, and the state of the microorganism cells trapped by the prior art purifying filter Dx of Comparative Example 7 which had no enzymes immobilized thereon are shown in electron micrographs in FIGS. 3 and 4, respectively. The electron micrographs were taken with a scanning electron microscope model S-4000 of Hitachi, Ltd. at an acceleration voltage of 5 kV.

FIG. 3 shows direct lysis of the cell walls of Bacillus subtilis which was arrested by the air purifying filter which had lysozyme immobilized in accordance with the invention. On the other hand, FIG. 4 shows that the conventional air purifying filter which had no enzymes immobilized thereon was incapable of killing microorganism cells but it just left them as trapped. The two electron micrographs obviously show the difference between the states of trapped cells and it was supported that the enzyme immobilized on the air purifying filter caused a sufficient lysing action on the retained microorganism cells to remove them by killing or otherwise controlling them.

Example 12

A filter paper-like carrier for use in a pseudo-HEPA filter (product of HOKUETSU PAPER MILLS, LTD.) which was composed of boron-silica glass fibers not rendered to be water repellent and which had an arrest efficiency of at least 99% in a 0.3 An monodisperse DOP test was immersed in a 100 mM phosphate buffer solution (pH 7) at room temperature for 30 minutes, recovered and had the excess water deposit removed. The filter paper-like carrier was then left in a 1% lysozyme containing aqueous solution (S3) at room temperature for 3 hours so as to immobilize the lysozyme on the filter paper-like carrier by an ionic bonding reaction. The filter paper-like carrier having the lysozyme immobilized thereon was further washed with a 100 mM phosphate buffer solution of pH 7 (S4); and upon air drying, the physical adsorption of the enzyme on the filter paper-like carrier was removed to leave only the lysozyme content that was immobilized through ionic bonding. The thus prepared filter was designated as air purifying filter F.

Comparative Example 9

The untreated filter paper-like carrier for use in a pseudo-HEPA filter which was used in Example 12 and which was composed of the boron-silica glass fibers not rendered to be water repellent was designated as air purifying filter Fx.

Test 6

The amount of residual lysozyme in the spent aqueous solution (S3A) resulting from the immobilization treatment by ionic bonding reaction in Example 12 and the amount of lysozyme eluted into the buffer solution (S4A) used to wash the filter paper-like carrier after immobilization were measured with a protein assay kit of Bio-Rad Laboratories at a wavelength of 595 nm using a spectrophotometer model UV-2100PC of Shimadzu Corp.; and the percent immobilization of protamine and/or lysozyme through covalent bonding to the prepared air purifying filter was calculated and the results are shown in Table 8.

TABLE 8

| Enzyme immobilization to filter, % | Residual cells in sample gas after passage through filter, % sample gas introduction time, hour | | No. of viable cells on filter (cells/5 cm$^2$) sample gas introduction time, hour | |
|---|---|---|---|---|
| | 2 | 24 | 2 | 24 |
| Example 12  90 | <0.01 | <0.01 | <3 | <3 |
| Comp. Ex. 9  — | 3.4 | 3.9 | >300 | >300 |

As is clear from the values of percent enzyme immobilization shown in Table 8, the air purifying filter F of Example 12 employing the filter paper-like carrier which was composed of the boron-silica glass fibers not rendered to be water repellent featured effective immobilization of high volume lysozyme although the binding force was ionic rather than covalency.

Table 8 shows the data for the percent residual cells in the gas from the air purifying filter as determined in Test 4 using the air purifying filters F and Fx of Example 12 and Comparative Example 9, respectively. As is clear from the values of percent residual cells, the air purifying filter F of Example 12 of the invention which employed the filter paper-like carrier for use in a pseudo-HEPA filter which was composed of the boron-silica glass fibers not rendered to be water repellent but which had lysozyme immobilized through ionic bonding showed at least about 300 times as great purification performance by killing organism cells as the air purifying filter Fx of Comparative Example 9.

Table 8 also shows the values of viable cell count per cm² on the air purifying filters F and Fx of Example 12 and Comparative Example 9, respectively, as determined in Test 5 after 2 hours of the sample gas introduction. As is clear from the values of viable cell count shown in Table 8, the air purifying filter F of Example 12 of the invention which was composed of the boron-silica glass fibers not rendered to be water repellent exhibited at least 100 times as great purification performance by killing the trapped microorganism cells as the filter of Comparative Example 9. Thus, it was verified that microorganism cells decreased rapidly in number after they were retained on the air purifying filter F which had lysozyme immobilized through ionic bonding in accordance with the invention. Further, the air purifying filter F of the invention maintained the bactericidal purification performance on the test air purifying filter even after 24 hours introduction of the sample gas, thereby demonstrating that the microorganism cells retained on the air purifying filter could be controlled over a prolonged time.

The foregoing results of Tests 4, 5 and 6 demonstrate: the air purifying filter F of the invention which had lysozyme immobilized through ionic bonding could maintain as high bactericidal purification performance by adsorbing microorganism cells and lysing their cell walls as in the case of immobilization through the aforementioned covalent bonding; and immobilizing the large amount of lysozyme and the like effectively through ionic bonding contributed to the maintenance of even higher bactericidal purification performance over a prolonged time.

Example 13

A filter made of a nonwoven fabric of ion-exchange fibers having —$NH_2$ functional groups and an average diameter of 30 $\mu$m was immersed in a 100 mM phosphate buffer solution (pH 7) at room temperature for 30 minutes, recovered and had the excess water deposit removed. The resulting filter was immersed in a 2.5% aqueous glutaraldehyde solution at room temperature for one hour so as to introduce aldehyde groups into the nonwoven fabric filter made of ion-exchange fibers. The filter having the aldehyde groups introduced therein was further washed with a buffer solution (pH 7) prepared by mixing a 100 mM NaCl solution with a 100 mM acetic acid solution, and then the filter was left in an aqueous solution (S5) containing 1% polylysine and 1% lysozyme for 3 hours so that protamine and lysozyme were immobilized on the filter. The nonwoven fabric filter made of the ion-exchange fibers having both polylysine and lysozyme immobilized thereon was further washed with a buffer solution of pH 7 (S6) prepared by mixing a 100 mM NaCl solution with a 100 mM acetic acid solution; and upon air drying, the physical adsorption of the enzyme on the nonwoven fabric filter was removed to leave only the polylysine and lysozyme contents that were immobilized through covalent bonding. The thus prepared filter was designated as air purifying filter G.

Comparative Example 10

The untreated filter used in Example 13 which was made of a nonwoven fabric of ion-exchange fibers having —$NH_2$ functional groups and an average diameter of 30 $\mu$m was designated as air purifying filter Gx.

Example 14

A filter made of a nonwoven fabric of ion-exchange fibers having —COOH functional groups and an average diameter of 30 $\mu$m was immersed in a 100 mM phosphate buffer solution (pH 7) at room temperature for 30 minutes, recovered and had the excess water deposit removed. The filter was then left in an aqueous solution (S7) containing 1% polylysine and 1% lysozyme for 3 hours at room temperature so that the polylysine and lysozyme were immobilized by an ionic bonding reaction. The nonwoven fabric filter made of the ion-exchange fibers having both polylysine and lysozyme immobilized thereon was further washed with a 100 mM phosphate buffer solution of pH 7 (S8); and upon air drying, the physical adsorption of the enzyme on the nonwoven fabric filter was removed to leave only the polylysine and lysozyme contents that were immobilized through covalent bonding. The thus prepared filter was designated as air purifying filter H.

Comparative Example 11

The untreated filter used in Example 14 which was made of a nonwoven fabric of ion-exchange fibers having —COOH functional groups and an average diameter of 30 $\mu$m was designated as air purifying filter Hx.

Test 7

The amounts of residual polylysine and lysozyme in the spent aqueous solutions (S5A and S7A) resulting from the immobilization treatment conducted by covalent bonding and ionic bonding reactions in Examples 13 and 14, respectively, as well as the amounts of polylysine and lysozyme eluted into the buffer solutions (S6A and S8A) used to wash the filter paper-like carriers after immobilization were measured with a protein assay kit of Bio-Rad Laboratories at a wavelength of 594 nm using a spectrophotometer model UV-2100PC of Shimadzu Corp.; and the percent immobilization of polylysine and lysozyme through covalent bonding or ionic bonding to the prepared air purifying filters was calculated and the results are shown in Table 9.

TABLE 9

| | Enzyme immobilization to filter, % | Residual cells in sample gas after passage through filter, % sample gas introduction time, hour | | No. of viable cells on filter (cells/5 cm²) sample gas introduction time, hour | |
| --- | --- | --- | --- | --- | --- |
| | | 2 | 24 | 2 | 24 |
| Example 13 | 81 | 1.2 | 1.2 | <3 | <3 |
| Comp. Ex. 10 | — | 65 | 67 | >300 | >300 |
| Example 14 | 86 | 1.1 | 1.1 | <3 | <3 |
| Comp. Ex. 11 | — | 67 | 71 | >300 | >300 |

As is clear from Table 9, the air purifying filter G of Example 13 of the invention which was prepared from the nonwoven fabric of ion-exchange fibers having —$NH_2$ functional groups and the air purifying filter H made from the nonwoven fabric of ion-exchange fibers having —COOH functional groups and an average diameter of 30 $\mu$m had large amounts of polylysine and lysozyme immobilized through effective bonding.

Table 9 also shows the data for percent residual cells in the gas from the air purifying filter as measured in Test 4 (accelerated test to evaluate bactericidal performance) using air purifying filters G and H of Examples 13 and 14, as well as air purifying filters Gx and Hx of Comparative Examples 10 and 11. As is clear from the values of percent residual cells in the gas from the air purifying filter, the air purifying filter G and H of Examples 13 and 14 of the invention which were prepared from the nonwoven fabrics of ion-exchange fibers having functional groups to which lysozyme and the like were immobilized through covalent bonding or ionic bonding exhibited far superior purification performance by killing microorganism cells as compared to the air purifying filters Gx and Hx of Comparative Examples 10 and 11 which were prepared from the nonwoven fabrics of ion-exchange fibers having functional groups but which had no enzymes immobilized thereon.

Table 9 also gives data for the number of viable cells per 5 $cm^2$ on the air purifying filter as determined in Test 5 for the air purifying filters G and H of Examples 13 and 14, as well as the air purifying filters Gx and Hx of Comparative Examples 10 and 11 after 2 hours of the sample gas introduction. As is clear from the values of viable cell count shown in Table 9, the air purifying filters G and H of Examples 13 and 14 of the invention which were prepared from the nonwoven fabrics of ion-exchange fibers having polylysine and lysozyme immobilized uniformly also excelled in purification performance by killing or otherwise controlling the microorganism cells trapped on the filter. Further, the air purifying filters G and H of the invention maintained the bactericidal purification performance on the air purifying filters even after 24 hours of the sample gas introduction, and thereby it was demonstrated that the microorganism cells retained on the filters could be controlled over a prolonged time.

The foregoing results of Tests 4, 5 and 7 demonstrate: the air purifying filters G and H of the invention maintained high bactericidal purification performance by adsorbing microorganism cells and lysing their cell walls by means of the lysozyme and the like which were immobilized through covalent bonding and/or ionic bonding; and the immobilization of the large amount of lysozyme and the like effectively through covalent bonding and/or ionic bonding contributed to the maintenance of even higher bactericidal purification performance over a prolonged time.

Comparative Example 12

A filter paper-like carrier for use in a pseudo-HEPA filter (product of HOKUETSU PAPER MILLS, LTD.) which was composed of boron-silica glass fibers not rendered to be water repellent and which had an arrest efficiency of at least 99% in a 0.3 μm monodisperse DOP test was immersed at room temperature for 30 min in an aqueous solution prepared by diluting a 50% aqueous polyitaconic acid solution (product of Iwata Kagaku Kogyo K.K.) 10 folds with water, and thereafter the carrier was recovered and had the excess water deposit removed. The excess water-free carrier was then dried for one hour in a dryer held at a temperature of 60° C. The thus prepared filter was designated as air purifying filter Ix. Identification of the prepared air purifying filter Ix with an electron microscope model JSM5300 of JEOL LTD. and a Fourier-transformer spectrophotometer model JIR-WINSPEC 50 of JEOL LTD. verified uniform coating thereon with a polymer having —COOH functional groups.

Example 15

The air purifying filter Ix prepared in Comparative Example 12 with a uniform coat of the polymer having —COOH functional groups was immersed in a 100 mM phosphate buffer solution (pH 7) at room temperature for 30 minutes, and thereafter recovered and had the excess water deposit removed. The resulting air purifying filter Ix which was coated uniformly with the polymer having —COOH functional groups was left in an aqueous solution (S9) containing 0.5% lysozyme and 0.5% chitinase for 3 hours at room temperature so that both lysozyme and chitinase were immobilized by an ionic bonding reaction. The air purifying filter having the lysozyme and chitinase immobilized thereon was further washed with a 100 mM phosphate buffer solution of pH 7 (S10); and upon air drying, the physical adsorption of the enzymes on the filter paper-like carrier was removed to leave only the lysozyme and chitinase contents that were immobilized through ionic bonding. The thus prepared filter was designated as air purifying filter I.

Comparative Example 13

A filter paper-like carrier for use in a pseudo-HEPA filter (product of HOKUETSU PAPER MILLS, LTD.) which was composed of boron-silica glass fibers not rendered to be water repellent and which had an arrest efficiency of at least 99% in a 0.3 μm monodisperse DOP test was immersed at room temperature for 30 minutes in an aqueous solution prepared by diluting a 50% aqueous polyallylamine (product of NITTO BOSEKI CO., LTD.) 10 folds with water, and thereafter was recovered and had the excess water deposit removed. The excess water-free carrier was then dried for one hour in a dryer held at a temperature of 60° C. The thus prepared filter was designated as air purifying filter Jx. Identification of the prepared air purifying filter Jx with an electron microscope model JSM-5300 of JEOL LTD. and a Fourier-transformer spectrophotometer model JIR-WINSCPEC 50 of JEOL LTD. verified uniform coating thereon with a polymer having —$NH_2$ functional groups.

Example 16

The air purifying filter Jx prepared in Comparative Example 13 with a uniform coat of the polymer having —$NH_2$ functional groups was immersed in a 500 mM phosphate buffer solution (pH 7) at room temperature for 30 minutes and subsequently immersed in a 2.5% aqueous glutaraldehyde solution at room temperature for one hour so that aldehyde groups were introduced into the air purifying filter Jx uniformly coated with the polymer having —$NH_2$ functional groups. The air purifying filter uniformly coated with the polymer having —$NH_2$ functional groups into which aldehyde groups were introduced was further washed with a buffer solution (pH 7) prepared by mixing a 500 mM NaCl solution with a 500 mM acetic acid solution; and thereafter the filter was left for 3 hours in an aqueous solution (S11) containing 0.5% lysozyme and 0.5% chitinase so that both the lysozyme and chitinase were immobilized on the filter. The air purifying filter uniformly coated with the polymer having —$NH_2$ functional groups into which aldehyde groups were introduced and which had lysozyme and chitinase immobilized thereon was further washed with a buffer solution (S12) of pH 7 prepared by mixing a 500 mM NaCl solution and a 500 mM acetic acid solution; and upon air drying, the physical adsorption of the enzymes on the air purifying filter uniformly coated with the polymer having —$NH_2$ functional groups into which aldehyde groups were introduced was removed to leave only the lysozyme and chitinase contents that were immobilized through covalent bonding. The thus prepared filter was designated as air purifying filter J.

Test 8

The amounts of residual lysozyme and chitinase in the spent aqueous solutions (S9 and S11) resulting from the immobilization treatments conducted through ionic bonding and covalent bonding in Examples 15 and 16, respectively, as well as the amounts of lysozyme and chitinase eluted into the buffer solutions (S10 and S12) used to wash the filter paper-like carriers after immobilization were measured with a protein assay kit of Bio-Rad Laboratories at a wavelength of 595 nm using a spectrophotometer model UV-2100PC of Shimadzu Corp.; and the percent immobilization of lysozyme and chitinase through ionic bonding and/or covalent bonding to the prepared air purifying filters were calculated and the results are shown in Table 10.

TABLE 10

|  | Enzyme immobilization to filter, % | Residual cells in sample gas after passage through filter, % sample gas introduction time, hour | | No. of viable cells on filter (cells/5 cm²) sample gas introduction time, hour | |
|---|---|---|---|---|---|
|  | % | 2 | 24 | 2 | 24 |
| Example 15 | 92 | <0.01 | <0.01 | <3 | <3 |
| Comp. Ex. 12 | — | 63 | 66 | >300 | >300 |
| Example 16 | 91 | <0.01 | <0.01 | <3 | <3 |
| Comp. Ex. 13 | — | 65 | 68 | >300 | >300 |

As is clear from Table 10, the air purifying filter I of Example 15 of the invention which was prepared from the filter paper-like carrier with a uniform coating of the polymer having —COOH functional groups and the air purifying filter J of Example 16 which was prepared from the filter paper-like carrier with a uniform coating of the polymer having —NH$_2$ functional groups had large amounts of lysozyme and chitinase immobilized through uniform bonding.

Table 10 also shows the data for percent residual cells in the gas from the air purifying filter as measured in Test 4 (accelerated test to evaluate bactericidal performance) using the air purifying filters I and J of Examples 15 and 16, as well as the air purifying filters Ix and Jx of Comparative Examples 12 and 13. As is clear from the values of percent residual cells in the gas from the air purifying filter, the air purifying filters I and J of Examples 15 and 16 of the invention which were prepared from the filter paper-like carriers with a uniform coating of the polymer having functional groups to which lysozyme and chitinase were immobilized through ionic bonding and covalent bonding exhibited far superior purification performance by killing organism cells as compared to the air purifying filters Ix and Jx of Comparative Examples 12 and 13 which were prepared from the filter paper-like carriers with a uniform coating of the polymer having functional groups but which had no enzymes immobilized thereon.

Table 10 also gives data for the number of viable cells per 5 cm² on the test air purifying filter as determined in Test 5 for air purifying filters I and J of Examples 15 and 16, as well as air purifying filters Ix and Jx of Comparative Examples 12 and 13 after 2 h of sample gas introduction. As is clear from the values of viable cell count shown in table 10, the air purifying filters I and J of Examples 15 and 16 of the invention which were prepared from the filter paper-like carriers having a uniform polymer coat with lysozyme and chitinase immobilized uniformly thereon also excelled in purification performance by killing or otherwise controlling the microorganism cells trapped on the filter. Further, the air purifying filters I and J of the invention maintained the bactericidal purification performance on the filters even after 24 hours of the sample gas introduction, and thereby it was demonstrated that the microorganism cells retained on the filters could be controlled over a prolonged time.

The foregoing results of Tests 4, 5 and 8 demonstrate: the air purifying filters I and J of the invention maintained high bactericidal purification performance by adsorbing microorganism cells and lysing their walls by means of the lysozyme and the like which were immobilized through covalent bonding and/or ionic bonding; and the immobilization of the large amount of lysozyme and the like effectively through covalent bonding and/or ionic bonding contributed to the maintenance of even higher bactericidal purification performance over a prolonged time.

Test 9

As in Tests 4 and 5, the number of viable cells in each 5 cm² area of the test air purifying filter was determined at 2 hours intervals for an expanded microorganism spectrum including not only Bacillus subtilis (ATCC 6633) but also Micrococcus luteus (ATCC 9341), Staphylococcus aureus (IFO 13276), Escherichia coli (ATCC 10536), Vibrio parahaemolyticus (IFT 12970) and a blue mold (Penicillium roqueforti, IFO 5459). The results are shown in Table 11.

TABLE 11

Bactericidal Test on Various Microorganisms

|  | Comp. Ex. 7 | Ex. 4 | Ex. 5 | Ex. 6 | Ex. 7 |
|---|---|---|---|---|---|
| * Gram-positive organisms |  |  |  |  |  |
| Bacillus subtilis ATCC 6633 | >300 | <3 | <3 | <3 | <3 |
| Micrococcus luteus ATCC 9341 | >300 | <3 | <3 | <3 | <3 |
| Staphylococcus aureus IFO 13276 | >300 | <3 | <3 | <3 | <3 |
| * Gram-negative organisms |  |  |  |  |  |
| Escherichia coli ATCC 10536 | >300 | 21 | <3 | 15 | <3 |
| Vibrio parahaemolyticus IFO 12970 | >300 | 88 | 8 | <3 | <3 |
| * Mold |  |  |  |  |  |
| Penicillium roqueforti IFO 5459 | >300 | 58 | <3 | <3 | <3 |

(Notes)

Comparative Example 7 (Dx) Filter alone

Example 4 (D1): Lysozyme immobilized on filter

Example 5 (D2): Lysozyme+protamine immobilized on filter

Example 6 (D3): Lysozyme+glucan immobilized on filter

Example 7 (D4): Lysozyme+protamine+glucan immobilized on filter

As is clear from Table 11, the air purifying filter D2 of Example 5 having lysozyme immobilized in combination with protamine, the air purifying filter D3 of Example 6 having lysozyme immobilized in combination with glucan and the air purifying filter D4 of Example 7 having lysozyme immobilized in combination with protamine and glucan had an enhanced bactericidal effect against Gram-negative Escherichia coli and Vibrio parahaemolyticus and a mold Penicillium roqueforti compared to the air purifying filter D1 of Example 4 which had only lysozyme immobilized on the filter. Briefly, it was supported that by using bactericidal enzymes in combination with either non-enzyme proteins or peptides also having a bactericidal action or with polysaccharides, the ability of the filter to purify air by killing or otherwise controlling microorganisms can be enhanced in terms of the wider lysing spectrum.

Industrial Applicability

The air purifying filter of the invention is capable of an efficient adsorption of air-borne bacteria, fungi and other microorganisms that have been impossible to remove by the conventional filters, and a high bactericidal purification performance by killing the microorganisms through direct lysis of their cell walls, as well as prolonged bactericidal purification of air. In addition, the filter is capable of removing the retained organism cells by killing or otherwise controlling them so that they will not regrow to thereby prevent the microbial deterioration of the filter carrier and secondary contamination due to the scattering of the organism cells. For removing microorganisms in food, cosmetic, microelectronics, medical and other fields, there is no alternative to using ULPA and HEPA filters which are ultrahigh- and high-performance filters primarily intended for removing fine dust particles and which hence require huge electrical energy consumption to compensate for large pressure loss from air supply. If the air purifying filter of the invention is used as a filter element, a low-pressure loss filter downgraded by several classes can be realized and it can be used as a low environmental impact filter requiring no more than a fraction of the heretofore required electrical energy consumption.

What is claimed is:

1. An air purifying filter comprising:
    a carrier; and
    an enzyme immobilized on a surface of the carrier and having a lysing action that achieves bacteriocidal air purification and kills microorganisms through direct lysis of cell walls of the microorganisms that are trapped on the surface of the carrier,
    wherein the surface of the carrier has not been rendered to be water repellent prior to immobilizing the enzyme on the surface of the carrier.

2. The air purifying filter according to claim 1, wherein the enzyme is at least one lysing enzyme selected from among lysozyme, chitinase, protease, glucose oxidase, glucanase, b-galactosidase, end-b-N-acetylglucosaminidase and endolysin.

3. The air purifying filter according to claim 1, wherein the enzyme is either of a single type or a system consisting of two or more types, or it forms a mixture or a compound with a non-enzyme protein or peptide and/or a polysaccharide.

4. The air purifying filter according to claim 3, wherein the non-enzyme protein or peptide is one bactericidal protein or peptide selected from among protamine, lactoferrin and polylysine.

5. The air purifying filter according to claim 3, wherein the polysaccharide is one of glucan, dextran, mannan, galactomannan, laminaran, carrageenan and agarose.

6. The air purifying filter according to claim 3, wherein the enzyme is at least one lysing enzyme selected from among lysozyme, chitinase, protease, glucose oxidase, glucanase, b-galactosidase, end-b-N-acetylglucosaminidase and endolysin.

7. The air purifying filter according to claim 1, wherein a percentage of enzyme immobilization on the filter is greater than or equal to 80% of the enzyme to which the filter was exposed.

8. The air purifying filter according to claim 1, wherein the filter comprises a filter capable of arresting at least 99.97% of 0.3 $\mu$m DOP particles.

9. The air purifying filter according to claim 1, wherein the enzyme is immobilized through ionic bonding.

10. The air purifying filter according to claim 9, wherein the filter comprises a filter capable of arresting at least 99.97% of 0.3 $\mu$m DOP particles.

11. The air purifying filter according to claim 1, wherein the enzyme is immobilized through covalent bonding.

12. The air purifying filter according to claim 11, wherein the filter comprises a filter capable of arresting at least 99.97% of 0.3 $\mu$m DOP particles.

13. The air purifying filter according to claim 1, wherein the air filter comprises a filter capable of arresting at least 95% of 0.3 $\mu$m DOP particles.

14. The air purifying filter according to claim 1, wherein the carrier comprises glass fibers.

15. The air purifying filter according to claim 14, wherein the enzyme is immobilized through covalent bonding.

16. The air purifying filter according to claim 14, wherein the filter comprises a filter capable of arresting at least 99.97% of 0.3 $\mu$m DOP particles.

17. The air purifying filter according to claim 14, wherein the glass fibers comprise boron-silica glass fibers.

18. The air purifying filter according to claim 17, wherein the enzyme is immobilized through covalent bonding.

19. The air purifying filter according to claim 17, wherein the enzyme is immobilized through ionic bonding.

20. The air purifying filter according to claim 17, wherein the filter comprises a filter capable of arresting at least 99.97% of 0.3 $\mu$m DOP particles.

21. The air purifying filter according to claim 17, wherein the boron-silica glass fibers are coated with a polymer having a functional group.

22. The air purifying filter according to claim 21, wherein the polymer having a functional group is a polymer having at least one functional group selected from among —NHR (R is not H but an alkyl group selected from among methyl, ethyl, propyl and butyl), —NH$_2$, —C$_6$H$_5$NH$_2$, CHO, —COOH and —OH.

23. The air purifying filter according to claim 22, wherein the enzyme is immobilized through ionic bonding.

24. The air purifying filter according to claim 21, wherein the enzyme is immobilized through ionic bonding.

25. The air purifying filter according to claim 1, wherein the carrier is one of cellulose fibers, asbestos fibers, and ion-exchange fibers.

26. The air purifying filter according to claim 25, wherein the enzyme is immobilized through ionic bonding.

27. The air purifying filter according to claim 25, wherein the enzyme is immobilized through covalent bonding.

28. The air purifying filter according to claim 25, wherein the filter comprises a filter capable of arresting at least 99.97% of 0.3 $\mu$m DOP particles.

29. An air purifying filter comprising:
    a carrier comprising ion-exchange fibers; and
    an enzyme immobilized on a surface of the carrier, the enzyme having a lysing action that achieves bacteriocidal air purification and kills microorganisms through direct lysis of cell walls of the microorganisms cells that are trapped on the surface of the carrier,
    wherein the carrier has not been rendered to be water repellent prior to immobilizing the enzyme on the carrier.

30. The air purifying filter of claim 29 wherein the ion-exchange fibers are coated with a polymer having a functional group.

31. An air purifying filter comprising:
    a carrier comprising boron-silica glass fibers coated with a polymer having a functional group; and an enzyme immobilized on a surface of the carrier, the enzyme having a lysing action that achieves bacteriocidal air purification and kills microorganisms through direct lysis of cell walls of the microorganisms cells that are trapped on the surface of the carrier, wherein the carrier has not been rendered to be water repellent prior to immobilizing the enzyme on the carrier, and a percentage of enzyme immobilization on the surface of the carrier is greater than 80% of the enzyme to which the filter was exposed.

32. A method of fabricating an air purifying filter comprising:

providing a carrier that has not been rendered to be water repellent; and immobilizing an enzyme on a surface of the carrier, wherein the enzyme has a lysing action that achieves bacteriocidal air purification and kills microorganisms through direct lysis of cell walls of the microorganisms that are trapped on the surface of the carrier.

33. The method of fabricating an air purifying filter of claim 32, wherein immobilizing the enzyme comprises immobilizing the enzyme through covalent bonding.

34. The method of fabricating an air purifying filter of claim 32, wherein immobilizing the enzyme comprises immobilizing the enzyme through ionic bonding.

35. The method of fabricating an air purifying filter of claim 32, wherein immobilizing comprises immobilizing the enzyme on the surface of the carrier at a percentage of enzyme immobilization at not less than 80% of the enzyme to which the filter was exposed.

36. The method of fabricating an air purifying filter according to claim 32 wherein immobilizing an enzyme comprises immersing the carrier in an aqueous solution comprising protamine and lysozyme.

37. The method of fabricating an air purifying filter according to claim 36 wherein the aqueous solution comprises 1% protamine and 1% lysozyme.

38. The method of fabricating an air purifying filter according to claim 36 wherein the aqueous solution further comprises glucan.

39. The method of fabricating an air purifying filter according to claim 38 wherein the aqueous solution comprises 1% protamine, 1% lysozyme, and 0.2% glucan.

40. A method of purifying air of bacteria, the method comprising:

providing an air purifying filter comprising fibers having a surface and space between the fibers and an enzyme immobilized on the surface of the fibers, the enzyme having a lysing action that achieves bacteriocidal air purification, wherein the surface of the fibers has not been treated to be water repellent prior to immobilizing the enzyme on the surface of the fibers;

passing air containing microorganism cells through the air purifying filter, whereby the space between the fibers comprises air and microorganism cells trapped on the fibers; and lysing at least a portion of cell walls of the microorganism cells trapped on the fibers as the air passes through the air purifying filter.

41. The method of purifying air of bacteria according to claim 40, wherein the bacteria is captured on the air purifying filter and killed by the lysing action of the enzyme, whereby the captured bacteria does not pass out of the air purifying filter.

42. The method of purifying air of bacteria according to claim 40, wherein the fibers comprise one or more of glass fibers, cellulose fibers, asbestos fibers, and ion-exchange fibers.

43. The method of purifying air of bacteria according to claim 40, wherein the enzyme is immobilized through covalent bonding.

44. The method of purifying air of bacteria according to claim 40, wherein the enzyme is immobilized through ionic bonding.

45. The method of purifying air of bacteria according to claim 40, wherein the filter comprises a filter capable of arresting at least 99.97% of 0.3 $\mu$m DOP particles.

46. The method of purifying air of bacteria according to claim 40, wherein the enzyme comprises one or more of at least one lysing enzyme selected from among lysozyme, chitinase, protease, glucose oxidase, glucanase, $\beta$-galactosidase, end-$\beta$-N-acetylglucosaminidase and endolysin.

* * * * *